United States Patent [19]
Chang et al.

[11] Patent Number: 5,753,723
[45] Date of Patent: May 19, 1998

[54] DENTURE FIXATIVE WITH AN ADHESION PROMOTER

[76] Inventors: Tiang Shing Chang, 1016 Seward Ave., Westfield, N.J. 07090; Donna Diferdinando, 307 Arlington Ave., Union Beach, N.J. 07735

[21] Appl. No.: 900,960

[22] Filed: Jul. 25, 1997

Related U.S. Application Data

[63] Continuation of Ser. No. 568,051, Dec. 6, 1995, abandoned.

[51] Int. Cl.$^6$ ............................ C09J 3/04; A61K 5/06
[52] U.S. Cl. ............... 523/120; 524/42; 524/239; 524/321; 524/549; 524/559; 514/574; 106/35
[58] Field of Search ............... 523/120; 524/42, 524/417, 239, 321, 549, 559; 514/574; 106/35

[56] References Cited

U.S. PATENT DOCUMENTS

| | | | |
|---|---|---|---|
| 3,003,988 | 10/1961 | Germann et al. | 523/120 |
| 3,553,314 | 1/1971 | Francis | 424/49 |
| 3,558,769 | 1/1971 | Globus | 424/49 |
| 3,737,522 | 6/1973 | Francis | 424/49 |
| 4,183,914 | 1/1980 | Gaffar et al. | 424/49 |
| 4,356,819 | 11/1982 | Potaczek | 523/111 |
| 4,373,036 | 2/1983 | Chang et al. | 523/120 |
| 4,521,551 | 6/1985 | Chang et al. | 523/120 |
| 4,569,955 | 2/1986 | Dhabhar et al. | 523/120 |
| 4,758,630 | 7/1988 | Shah et al. | 525/207 |
| 4,910,247 | 3/1990 | Holdar et al. | 524/400 |
| 4,980,391 | 12/1990 | Kumar et al. | 524/45 |
| 5,006,571 | 4/1991 | Kumar et al. | 523/120 |
| 5,037,924 | 8/1991 | Tazi et al. | 526/272 |
| 5,073,604 | 12/1991 | Holeva et al. | 523/327 |
| 5,093,387 | 3/1992 | Schobel et al. | 523/120 |
| 5,204,414 | 4/1993 | Pelah et al. | 525/327 |
| 5,298,534 | 3/1994 | Prosise et al. | 523/120 |
| 5,304,616 | 4/1994 | Rajaiah et al. | 526/240 |

*Primary Examiner*—Andrew E. C. Merriam

[57] ABSTRACT

An improved denture fixative composition comprising an adhesion promoter and a highly cross-linked copolymer of a lower alkyl vinyl ether and maleic anhydride or acid is disclosed wherein at least 65.0% of the total number of initial carboxyl groups in the copolymer are reacted. The cross-linking agent employed in this invention is calcium cation and optionally up to about 30.0% of the calcium function can be replaced with other inorganic cross-linking agents or polyhydroxy compounds either singly or in combination. The adhesion promoters are chelating agents such as polycarboxylic acids, hydroxycarboxylic acids, aminocarboxylic acids, polyphosphoric acids and their alkali salts.

20 Claims, No Drawings

DENTURE FIXATIVE WITH AN ADHESION PROMOTER

This is a continuation of application Ser. No. 08/568,051, filed Dec. 6, 1995 now abandoned.

FIELD OF THE INVENTION

The present invention relates generally to adhesive compositions for securing dentures and other dental prostheses to the gums of the oral cavity.

BACKGROUND OF THE INVENTION

There are a number of desirable characteristics for denture fixative compositions. One extremely desirable attribute is that it quickly generates tacky, uniform and viscous mucilages upon contact with saliva, so that the denture will be held in place as soon as it is seated in the mouth. It is also highly desirable that the mucilages possess sufficient cohesive strength to withstand the stress of mastication and to provide a cushion between the denture and its supporting gums or tissues during mastication. The denture fixative must also exhibit sufficient resistance to degradation under the environmental temperature changes which occur in the oral cavity during common actions such as drinking coffee or other hot beverages.

Many efforts have made over the years to develop an improved denture fixative composition. Both natural and synthetic hydrophilic polymers have been employed either singly or in combination and these have been formulated in liquid, powder, cream or film form. U.S. Pat. No. 3,003,988 to Germann et al. describes a denture fixative composition in which the denture fixative is a mixed partial salt containing calcium cations together with an alkali or quaternary ammonium cation of a lower alkyl vinyl ether-maleic anhydride copolymer or its partial lower alkyl esters. Many different denture fixative compositions have since been developed using this copolymer either in improved vehicles or in combination with other water soluble polymers or additives. Examples include U.S. Pat. Nos. 4,373,036 to Chang et al.; 4,514,528 and 4,569,955 to Dhabhar et al.; 4,910,247 to Holdar et al., 4,980,391 and 5,006,571 to Kumar et al.; 5,037,924 to Tazie et al. and 5,093,387 to Schobel et al.

Many derivatives of the lower alkyl vinyl ether and maleic anhydride or acid copolymer other than the sodium and calcium partial salts mentioned above have also been disclosed as effective denture fixative compositions. U.S. Pat. No. 4,521,551 to Chang et al. discloses and claims an effective denture fixative composition containing a partial salt of the alkali cation of a lower alkyl vinyl ether and maleic acid copolymer which is also partly cross-linked with polyhydroxy compounds. U.S. Pat. No. 4,758,630 to Shah et al. teaches an effective denture fixative composition comprised of the zinc or strontium partial salts of a lower alkyl vinyl ether and maleic acid copolymer wherein the said zinc and strontium cations are "unmixed" with any other cations or ester functions in the copolymer salt. Also, U.S. Pat. No. 5,073,604 to Holeva et al. discloses zinc or strontium partial salts of a lower alkyl vinyl either and maleic acid copolymer wherein the said zinc and strontium are "mixed" with calcium cation and optionally sodium cation in the copolymer salt. U.S. Pat. No. 5,304,616 to Rajaiah et al. further teaches the mixed salts of sodium, iron, strontium and zinc cation of a lower alkyl vinyl ether and maleic acid copolymer as effective denture fixatives. Another recent disclosure, U.S. Pat. No. 5,204,414 to Pelah et al. describes the use of a trivalent metal salt in which aluminum is combined with calcium and/or sodium cation so as to react with a lower alkyl vinyl ether and maleic acid copolymer to form an effective denture fixative.

It has now been discovered that the adhesion of the cross-linked derivatives of a lower alkyl vinyl ether and maleic anhydride or acid copolymer, wherein at least 65.0% of the total number of initial carboxyl groups in the copolymer are reacted, can be further promoted by incorporating a chelating agent such as polycarboxylic acids, hydroxycarboxylic acids, aminocarboxylic acids, polyphosphoric acids, and their alkali salts in the fixative compositions. When in contact with water or saliva, the fixative composition quickly forms a tacky, viscous and uniform mucilage which can be spread easily over the denture-mucosa interface to fill the gaps and therein provides not only a strong fixative property but also a cushion between the denture and its supporting gums and tissues.

Accordingly, it is the objective of this invention to provide new and improved denture fixative compositions, which contain a highly cross-linked derivative of a lower alkyl vinyl ether-maleic anhydride or acid copolymer and an adhesion promoter. The composition develops adhesiveness quickly and exhibits sufficient cohesive strength to withstand the stress of mastication, resists degradation from the environmental temperature changes which occur in the oral cavity and provides a cushion between the denture and its supporting gums and tissues. This and other objectives of this invention will become apparent to those skilled in the art from the following detailed description.

SUMMARY OF THE INVENTION

The present invention relates to denture fixative compositions in powder, liquid, cream, film and gel form. More particularly, the denture fixative compositions contain an adhesion promoter and a highly cross-linked derivative of a lower alkyl vinyl ether-maleic anhydride or maleic acid copolymer wherein at least 65.0% of the total number of initial carboxyl groups in the copolymer are reacted. The primary cross-linking agent employed in this invention is calcium cation and optionally up to about 30.0% of the calcium function in the copolymer can be replaced, either singly or in combination, by other inorganic or organic cross-linking agents. The adhesion promoters are chelating agents, such as polycarboxylic acids, hydroxycarboxylic acids, aminocarboxylic acids, polyphosphoric acid, their alkali salts and the like. This invention also relates to denture fixative compositions comprised of the above disclosed fixative composition and at least one hydrophilic polymer, in powder, liquid, cream, film and gel form. The preferable hydrophilic polymers are sodium carboxymethylcellulose, polyethylene oxide and sodium alginate.

DETAILED DESCRIPTION OF THE INVENTION

The polymeric fixatives of the present invention are the cross-linked derivatives of a lower alkyl vinyl ether maleic anhydride or maleic acid copolymer (AVE/MA). The AVE/MA copolymer used in the present invention has a specific viscosity not less than 1.5 and preferably is in the range of about 1.8 to about 4.0. Such copolymers have the repeating structural unit:

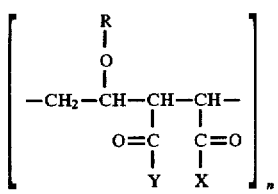

where X and Y each separately represent a hydroxyl moiety or together represent a single oxygen. R represents a lower alkyl moiety of from about 1 to about 5 carbon atoms, and n is large enough to provide the copolymers with a specific viscosity greater than 1.5. The copolymers are obtained by copolymerizing a lower alkyl vinyl ether monomer with maleic acid or maleic anhydride, and also can contain mixtures of the alkyl vinyl ethers. Suitable copolymers are commercially available such as GANTREZ® S series (acid form) and GANTREZ® AN series (anhydride form) produced by ISP Investments Inc. of Delaware.

The copolymer derivatives employed in the present invention are cross-linked such that at least about 65% of the total number of initial carboxyl groups in the copolymer are reacted either with calcium alone or optionally in combination with other cross-linking agents, in amounts up to about 30.0% of the calcium groups. In determining the total number of initial carboxyl groups, the anhydride radical is considered as having two such groups. The 1.0% aqueous solution of the cross-linked copolymer disclosed in the present invention should have a pH of at least 4.3 and preferably in the range from about 4.5 to about 6.5.

The anionic portion of the calcium salt is not restricted although it is preferably in the form of an oxide, hydroxide, carbonate or halide. The other optional cross-linking agents are either inorganic cations such as preferably zinc, strontium, and magnesium or organic cross-linking agents, preferably, polyhydroxy compounds such as propylene glycol, dipropylene glycol, glycerin, ethylene glycol, diethylene glycol, triethylene glycol, tetramethylene glycol, sorbitol and the like and generally have from about 2 to about 6 carbon atoms. Most preferably, the polyhydroxy compounds are propylene glycol and glycerin.

To cross-link the AVE/MA copolymer in the present invention, the cross-linking agents and copolymer, in a total amount of about 10% of solid, are dispersed in water at ambient temperature. The dispersion is then mixed and/or heated to allow the completion of the reaction and to form a uniform, viscous solution. The reaction temperature varies, depending on the selection of the cross-linking agents and the form of the AVE/MA copolymer. In general, the cross-linking agents will react at room temperature with the copolymer in its acid form and will react at about 85° C. with the copolymer in its anhydride form. The solution can be dried either at temperatures of about 300° C. in about 10 minutes or at temperatures about 85° C. in about 10 to about 16 hours. The dried material, usually in a flake or sheet form, is milled and screened through a 100 mesh sieve.

Because of the high degree of cross-linking, the AVE/MA copolymer derivatives disclosed herein exhibit excellent cohesive strength with fair to good adhesive strength when formulated as a denture adhesive. Therefore, if one were able to improve the adhesive strength of these compositions, a truly superior fixative could be achieved. To this end, an adhesion promoter was sought to add to the fixative composition to improve the tackiness while maintaining the cohesive strength constant.

It has now been surprisingly discovered that the incorporation of a chelating agent such as a polycarboxylic acid, hydroxylcarboxylic acid, aminocarboxylic acid, polyphosphoric acid and their alkali salts in the fixative composition can generate extremely strong adhesion properties as soon as the fixative composition is in contact with water or saliva. This novel composition forms a uniform and viscous mucilage which provides sufficient cohesive strength to withstand the stress of mastication and also provides a cushion between the denture and its supporting gums or tissues during the mastication. Examples of suitable polycarboxylic acids are fumaric acid, maleic acid, succinic acid, glutaric acid. Suitable hydroxycarboxylic acids are those such as citric acid, gluconic acid, tartaric acid and the like while the aminocarboxylic acids such as aspartic acid, ethylene diaminetetraacetic acid, and their alkali salts, and mixtures thereof enhance the adhesion strength considerably. The polyphosphoric acids and their alkaline salts such as hexametaphosphric acid and sodium polyphosphate also function well as adhesion promoters. The preferred adhesion promoters useful in the present invention are citric acid, fumaric acid, glutaric acid, tartaric acid, aspartic acid, maleic acid, sodium citrate, potassium citrate and sodium polyphosphate, and the most preferred agents are fumaric acid, citric acid, aspartic acid, sodium citrate and sodium polyphosphate. These are incorporated in amounts of from about 0.01% to about 4.0% and preferably in amounts from about 0.05% to about 3.5% of the total denture fixative composition.

Each of the cross-linked AVE/MA copolymers in the present invention may be incorporated into the denture fixative compositions as the sole fixative component or in combination with other water-soluble polymers. Such amounts will vary depending on the particular AVE/MA copolymer and cross-linking agent used, the degree of the cross-linking desired, the amount of the adhesion promoter and the other constituents of the fixative compositions. In general, the total fixative amount is about 10.0 wt % to about 80.0 wt % of the fixative compositions, and preferably from about 15.0% to about 70.0 wt %. The suitable hydrophilic polymers include both the natural and synthetic gums, preferably sodium carboxymethylcellulose, polyethylene oxide and sodium alginate. The fixative and polymers may also be formulated as a complete denture adhesive incorporating waxes, oils, preservatives, flavoring agents, colorants, sweetening agents, viscosity modifiers and the like.

The waxes useful in formulating the fixative as a denture adhesive comprise both natural and synthetic waxes and include, without limitation, animal waxes such as beeswax, lanoline and shellac wax, vegetable waxes such as carnauba, candelilla and bayberry waxes and mineral waxes such as petroleum including paraffin, and microcrystalline waxes.

The oils useful in these formulations include, without limitation, mineral oil, vegetable oil such as corn, soybean, cottonseed, castor, palm and coconut oils and animal oil such as fish oil and oleic acid.

Flavoring agents well known to the denture adhesive art may also be added to the compositions of the present invention. These flavoring agents may be chosen from synthetic flavor oils and/or natural oils derived from plants, leaves, flowers, fruits and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, organte, lime and grapefruit, and fruit essences including apple, strawberry, cherry, grape, pineapple and so forth. The flavoring agent may be liquid, spray dried, encapsulated, sorbed on a carrier and combinations thereof. A preferred flavoring agent is peppermint oil, commercially available from Rose Mitchum. The amount of flavoring agent utilized may vary depending on such factors as flavor type, adhesive formulation and strength desired. In general, amounts of about 0.01% to about 5.0% by weight of the total denture adhesive composition are usable, with amounts of about 0.05% by weight of the total denture adhesive composition are usable, with amounts of about 0.05% to 0.15% being preferred.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl polycarbonate and phosphates. The parabens include the methyl, ethyl, propyl, and butyl esters of parahydroxybenzoic acid. Methyl paraben and propyl paraben are the preferred preservatives of the invention, preferably utilized in amount of about 0.03% to about 0.6% by weight of the total denture adhesive composition.

The denture adhesive compositions may also include the use of sweeteners well known in the art.

The sweetening agent may be selected from a wide range of materials including water-soluble agents, water-soluble artificial sweeteners, and dipeptide-based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e. sodium or calcium saccharin salts, cyclamate salts, acesulfame-K, sucralose and the like, and the free acid form of saccharin.

C. Dipeptide-based sweeteners such as L-aspartyl-L-phenylalanine methyl ester and materials described in U.S. Pat. No. 3,491,131, L-D-aspartyl-N-(2,2,4,4-tetramethyl-3-thietanyl-D-alaninamide hydrate) and the like.

In general, the amount of sweetener will vary with the desired amount of sweetener selected for a particular denture adhesive formulation. This amount may be about 0.001% to about 5% by weight of the final denture adhesive composition when using an easily extractable sweetener. The colorants useful in the present invention include the pigments such as titanium dioxide, and may also include dyes suitable for food, drug and cosmetic applications. These colorants are known as F.D.&C. dyes. The materials acceptable for the foregoing spectrum of use are preferably watersoluble. Illustrative examples include indigo dye, known as F.D.&C. Blue No. 2, which is the disodium salt of 5,5'-indigotindi-sulfonic acid. Similarly, the dye known as F.D.&C. Green No. 1, comprises a triphenylmethane dye and is the monosodium salt of the 4-(4-Methyl-p-sulfobenzylamino) diphenylmethylene)-(1-(N-ethyl-N-P-sulfobenzyl)-2 5-cyclohexadienimini).A full recitation of F.D.&C. and D.&C. colorants and their corresponding chemical structures may be found in the Kirk-Othmer Encyclopedia of Chemical Technology, 3rd Edition, Volume 5, at pages 561–595.

The vehicle viscosity modifiers useful herein include polyethylene, its derivatives and petrolatum.

When a mineral oil vehicle is employed, polyethylene is used as a thickening agent to provide a "synthetic petrolatum" vehicle, and thus is used to adjust the extrusion (application) properties of the finished composition. Polyisobutylene may also be used in conjunction with polyethylene to further enhance the viscosity properties of the vehicle. Alternatively, a stock petrolatum, with or without mineral oil, may be employed depending upon the specific handling qualities which are desired in the final product.

The remaining aqueous phase viscosity modifiers useful in the present invention (sodium alginate, sodium carboxymethylcellulose, etc.) belong to the gum block of the denture adhesive. These agents have some impact on the extrusion qualities of the adhesive, but generally they are functionally dormant until they are activated by saliva in the mouth.

In a preferred aspect of the invention, the denture adhesive base composition may further include at least one cream base material selected from the group consisting of petrolatum, natural and synthetic oils and mixtures thereof.

The denture adhesive composition may be in the form of a paste or powder mixture. The means for preparing such formulations is well known in the denture adhesive art.

The following examples are provided to better describe and set forth ways in which to prepare the denture adhesive compounds of the present invention. They are for illustration purposes only however, and it is recognized that minor changes and variations may be made to these compositions not contemplated herein. To the extent that any such changes do not materially affect the chemical make-up or functionality of the final product, such changes are considered to be within the spirit and scope of the invention as recited by the claims that follow.

EXAMPLE 1

A powder mixture of 100 parts of a commercially available AVE/MA anhydride copolymer (Gantrez AN® 169, having a specific viscosity of 3.0) and 36.7 parts of calcium hydroxide was charged to a reaction kettle containing 1200 parts of deionized water. The mixture was blended to uniform slurry and then heated, while being mixed, to 85° C., where it was maintained for five minutes. The reaction slurry was then cooled to about 65° C. The resulting viscous solution was then dried, milled and screened through a 100 mesh sieve. This calcium AVE/MA copolymer, designated as Ca(77)AVE/MA, had a packed density of 0.85 g/ml, a pH of 5.5 as a 1.0% aqueous solution and about 77.0% of carboxyl groups reacted.

A second cross-linked polymer formulation was prepared in the same manner, but this time citric acid was added as an adhesion promotor to compare the formulations relative bond strengths. The compositions were prepared in the following amounts:

| Ingredient | Weight Percentage | |
|---|---|---|
|  | Example 1A | Example 1B |
| Ca(77)AVE/MA | 40.10% | 40.10% |
| Petrolatum | 59.90% | 58.90% |
| Citric acid |  | 1.00% |

The holding profile was characterized by the shear bond strength determined at different durations of the hydration of the fixative composition, according to the following procedure.

An Instron Universal Testing Instrument, equipped with a 100 lbs. transducer was employed. The test sample was prepared by applying 0.15 g of the fixative composition on a 7.6 cm×2.5 cm acrylic slide, representing the denture surface, and then sandwiched it together, by applying finger pressure, with another identical acrylic slide which was covered with a damp wet cloth representing the oral mucosal. The shear bond strength (adhesive strength), which is defined as a maximum force in pounds required to separate the test sample, was measured every ten minutes for a total duration of fifty minutes. 0.1 g of water was added to the test sample after each measurement to simulate the salvia secretion in the oral environment.

The results given in the following table show that the holding profile of Example 1B is superior to that of Example 1A.

|  | Shear Bond Strength (lbs) | |
| --- | --- | --- |
| Duration of hydration (min.) | Example 1A | Example 1B |
| 10 | 0.15 | 0.16 |
| 20 | 0.58 | 0.66 |
| 30 | 1.07 | 1.00 |
| 40 | 0.74 | 0.95 |
| 50 | 0.90 | 1.02 |

EXAMPLE 2

Following the reaction procedure of Example 1, a calcium AVE/MA copolymer with about 85.0% of the initial carbonyl groups reacted was prepared. This copolymer was designated as Ca(85)AVE/MA and has a packed density of about 0.88 g/ml and a pH of 6.5 as a 1.0% aqueous solution. A second formulation was then prepared including fumaric acid as an adhesion promotor.

The following compositions were prepared for comparison purposes and tested.

|  | Weight Percentage | |
| --- | --- | --- |
| Ingredient | Example 2A | Example 2B |
| Ca(85)AVE/MA | 40.20% | 40.20% |
| Petrolatum | 59.80% | 58.60% |
| Fumaric acid |  | 1.20% |

The shear bond strengths of these compositions, measured according to the test procedure in Example 1, at different durations of hydration are given below:

|  | Shear Bond Strength (lbs) | |
| --- | --- | --- |
| Duration of hydration (min.) | Example 2A | Example 2B |
| 10 | 0.11 | 0.11 |
| 20 | 0.34 | 0.34 |
| 30 | 0.61 | 0.69 |
| 40 | 0.59 | 0.90 |
| 50 | 0.59 | 0.65 |

Once again, the formulation containing the adhesion promotor exhibited superior bond strength with increasing hydration.

EXAMPLE 3

A pre-mixed powder of 100 parts of a commercially available AVE/MA anhydride copolymer (Gantrez® AN 169, having a specific viscosity of 3.0), 31.0 parts of calcium hydroxide and 14.2 parts of strontium carbonate was discharged to a reaction kettle containing 1200 parts of deionized water. The mixture was agitated to an uniform slurry and then heated, while being mixed, to 85° C., where it was mixed for additional five minutes. The reaction mixture was cooled to about 65° C. and then raised to about 80° C. The resulting viscous solution was then dried, milled and screened through 100 mesh sieve. This AVE/MA copolymer, designed as Ca(65)Sr(15) AVE/MA, has a packed density of 0.86% g/ml and a pH of 6.3 as a 1.0% aqueous solution with about 80.0% of the initial carbonyl groups reacted; 65% groups reacted with calcium cation and 15% groups reacted with strontium cation. A second cross-linked fixative was prepared also including an adhesion promotor.

The following compositions were prepared for comparison purposes and tested.

|  | Weight Percentage | |
| --- | --- | --- |
| Ingredient | Example 3A | Example 3B |
| Ca(65)Sr(15)AVE/MA | 40.10% | 40.10% |
| Petrolatum | 59.90% | 58.90% |
| Sodium citrate |  | 1.00% |

The shear bond strengths of these compositions measured according to the test procedure in the Example 1 are given below:

|  | Shear Bond Strength (lbs) | |
| --- | --- | --- |
| Duration of hydration (min.) | Example 3A | Example 3B |
| 10 | 0.19 | 0.18 |
| 20 | 0.71 | 0.78 |
| 30 | 1.05 | 1.33 |
| 40 | 0.83 | 0.91 |
| 50 | 0.61 | 0.61 |

Again, the fixative with the adhesion promotor exhibits a greater degree of bond strength with increasing hydration.

EXAMPLE 4

A powder mixture of 100 parts of a commercially available AVE/MA anhydride copolymer (Gantrez AN® 169, having a specific viscosity of 3.0), 36.7 parts of calcium hydroxide and 4.2 parts of zinc oxide was charged to a reaction kettle containing 1200 parts of deionized water. Again the mixture was blended to an uniform slurry. The slurry was heated while being mixed, to 85° C., where it was maintained for an additional five minutes. The reaction mixture was cooled and cross-linking occurred at about 80° C., forming a fine precipitation where it was maintained for an additional five minutes. The water was decanted and the precipitation was transferred to a tray while the temperature of the wet mixture was about 80° C. This was dried in an oven at 95° C. for eight hours, milled and screened through a 100 mesh sieve. The resulting copolymer, designated as Ca(77)Zn(8) AVE/MA, has a packed density of 0.90 g/ml, a pH of 6.3 as a 1.0% aqueous solution and about 85.0% of the initial carbonyl groups reacted; 77.0% reacted with calcium cation and 8.0% reacted with zinc cation. As before, a second formulation was prepared also incorporating a citric acid adhesion promotor.

The following compositions for comparison purpose were prepared and tested.

| Ingredient | Weight Percentage | |
|---|---|---|
| | Example 4A | Example 4B |
| Ca(77)Sr(8)AVE/MA | 32.00% | 32.00% |
| Sodium carboxycellulose | 18.00% | 18.00% |
| Petrolatum | 30.00% | 30.00% |
| Mineral Oil | 18.80% | 17.80% |
| fumed silica | 1.20% | 1.20% |
| Citric acid | | 1.00% |

The shear bond strengths measured according to the testing procedure in Example 1 are given below:

| Duration of hydration (min.) | Shear Bond Strength (lbs) | |
|---|---|---|
| | Example 4A | Example 4B |
| 10 | 0.53 | 0.68 |
| 20 | 1.39 | 1.58 |
| 30 | 0.93 | 1.53 |
| 40 | 0.79 | 1.33 |
| 50 | 0.54 | 1.01 |

The AVE/MA fixative with the added adhesion promotor again gave superior results.

EXAMPLE 5

A pre-mixed powder of 100 parts of a commercially available AVE/MA anhydride copolymer (Gantrez® AN 169, having a specific viscosity of 3.0) and 36.7 parts of calcium hydroxide was charged to a reaction kettle containing 1200 parts of deionized water and 6.3 parts of propylene glycol. The mixture was blended to a uniform slurry. The slurry was heated while being mixed, to 85° C., where it was maintained for an additional five minutes. The reaction mixture was then cooled and cross-linking occurred at about 65° C. wherein a milky solution was formed. It became very viscous at 80° C. The solution was dried in an oven for about eight hours and milled and screened through 100 mesh sieve. The resulting copolymer, designated as Ca(77)PG(13) AVE/MA, has a packed density of 0.84 g/ml, a pH of 6.4 as a 1.0% aqueous solution and about 90.0% of the initial carboxyl groups were reacted; 77.0% reacted with calcium cation and 13.0% reacted with propylene glycol.

Two additional formulations were prepared using the Ca(77)PG(13) AVE/MA copolymer. One further comprised aspartic acid as the adhesion promotor and a second incorporated sodium polyphosphate in this junction as follows:

| Ingredient | Weight Percentage | | |
|---|---|---|---|
| | Example 5A | Example 5B | Example 5C |
| Ca(77)PG(13)AVE/MA | 40.10% | 40.10% | 40.10% |
| Sodium Polyphosphate | | 1.00% | |
| Aspertic acid | | | 2.00% |
| Petrolatum | 59.90% | 58.90% | 57.90% |

The shear bond strengths measured according to the testing procedure given in Example 1 are given below:

| Duration of hydration (min.) | Shear Bond Strength (lbs) | | |
|---|---|---|---|
| | Example 5A | Example 5B | Example 5C |
| 10 | 0.16 | 0.20 | 0.16 |
| 20 | 0.51 | 0.61 | 0.58 |
| 30 | 0.71 | 0.70 | 0.71 |
| 40 | 0.48 | 0.76 | 0.51 |
| 50 | 0.39 | 0.58 | 0.28 |

Clearly the formulation that included sodium polyphosphate exhibited the strongest adhesion characteristics.

Various changes and modifications can be made in the compositions of this invention without departing from the spirit and the scope thereof. It should be understood that the examples and the particular proportions and methods of procedure set forth are intended to be illustrative only and that the invention is to be limited only by the following claims.

What we claim is:

1. An improved denture adhesive fixative comprising:
   a. a lower alkyl vinyl ether maleic anhydride copolymer wherein at least 65% of the initial carboxyl groups are cross-linked;
   b. a chelating agent adhesion promoter selected from the group consisting of polycarboxylic acids, hydroxy carboxylic acids, amino carboxylic acids, polyphosphoric acids, their alkali salts and mixtures thereof; and
   c. a hydrophilic polymer.

2. The denture adhesive fixative of claim 1 herein said lower alkyl vinyl ether maleic anhydride is cross-linked with inorganic cross-linking agent selected from the group comprising inorganic cations, polyhydroxy compounds and mixtures thereof.

3. The denture adhesive fixative of claim 2 wherein said inorganic cation cross-linking agent is selected from the group consisting of calcium, zinc, strontium and magnesium and mixtures thereof.

4. The denture adhesive fixative of claim 2 wherein said polyhydroxy compounds are selected from the group comprising propylene glycol, dipropylene glycol, glycerin, ethylene glycol, diethylene glycol, triethylene glycol, tetramethylene glycol, sorbitol and mixtures thereof.

5. The denture adhesive fixative of claim 1 wherein said chelating agent is selected from the group consisting of polycarboxylic acids, hydroxycarboxylic acids, aminocarboxylic acids, polyphosphoric acids and their alkali salts.

6. The denture adhesive fixative of claim 1 wherein said chelating agent is selected from the group comprising citric acid, aspartic acid, ethylenediamine tetraacetic acid, fumaric acid, glutaric acid, tartaric acid, aspartic acid, succinic acid, maleic acid, hexameta-polyphosphoric acid, their alkali salts and mixtures thereof.

7. The denture adhesive fixative of claim 6 wherein said hydrophilic polymer is selected from the group consisting of natural and synthetic gums, sodium carboxymethylcellulose, polyethylene oxide, sodium alginate and mixtures thereof.

8. The denture adhesive fixative of claim 7 wherein said chelating agent is incorporated in said denture fixative in an amount ranging from about 0.01 wt % to about 4.0 wt % of the total weight of the fixative composition.

9. The denture adhesive fixative of claim 8 formulated as an adhesive further comprising waxes, oils, preservatives, flavoring agents, viscosity modifiers, sweeteners, colorants and mixtures thereof.

10. The improve denture adhesive of claim 9 formulated as a cream, paste, powder, liquid, film, or gel.

11. An improved denture adhesive fixative comprising:
   a. a lower alkyl vinyl ether-maleic acid copolymer wherein at least 65% of its initial carboxyl groups are cross-linked;
   b. a chelating agent adhesion promoter selected from the group consisting of polycarboxylic acids, hydroxy carboxylic acids, amino carboxylic acids, polyphosphoric acids, their alkali salts and mixtures thereof; and
   c. a hydrophilic polymer.

12. The denture adhesive fixative of claim 11 herein said lower alkyl vinyl ether maleic anhydride is cross-linked with an organic cross-linking agent selected from the group comprising inorganic cations, polyhydroxy compounds and mixtures thereof.

13. The novel denture adhesive fixative of claim 12 wherein said inorganic cation cross-linking agent is selected from the group consisting of calcium, zinc, strontium and magnesium and mixtures thereof.

14. The novel denture adhesive fixative of claim 12 wherein said polyhydroxy compounds are selected from the group comprising propylene glycol, dipropylene glycol, glycerin, ethylene glycol, diethylene glycol, triethylene glycol, tetramethylene glycol, sorbitol and mixtures thereof.

15. The denture adhesive fixative of claim 11 wherein said chelating agent is selected from the group consisting of polycarboxylic acids, hydroxycarboxylic acids, aminocarboxylic acids, polyphosphoric acids and their alkali metal salts.

16. The denture adhesive fixative of claim 11 wherein said chelating agent is selected from the group comprising citric acid, aspartic acid, ethylenediamine tetraacetic acid, fumaric acid, glutaric acid, tartaric acid, aspartic acid, succinic acid, maleic acid, hexameta-polyphosphoric acid, their alkali salts and mixtures thereof.

17. The denture adhesive fixative of claim 16 wherein said hydrophilic polymers selected from the group consisting of natural and synthetic gums, sodium carboxymethylcellulose, polyethylene oxide, sodium alginate and mixtures thereof.

18. The denture adhesive fixative of claim 17 wherein said chelating agent is incorporated in said fixative in an amount ranging from about 0.01 wt % to about 4.0 wt % of the total weight of the fixative composition.

19. The denture adhesive fixative of claim 18 formulated as an adhesive further comprising waxes, oils, preservatives, flavoring agents, viscosity modifiers, sweeteners, colorants and mixtures thereof.

20. The improve denture adhesive of claim 19 formulated as a cream, paste, powder, liquid, film or gel.

* * * * *